United States Patent [19]

von Halasz et al.

[11] 3,985,810

[45] Oct. 12, 1976

[54] PROCESS FOR PREPARING PERFLUORINATED ETHERS

[75] Inventors: Sigmar-Peter von Halasz, Kelkheim, Taunus; Friedhelm Kluge, Frankfurt am Main, both of Germany

[73] Assignee: Hoechst Aktiengesellschaft, Frankfurt am Main, Germany

[22] Filed: Oct. 28, 1975

[21] Appl. No.: 626,349

[30] Foreign Application Priority Data

Oct. 30, 1974 Germany............................ 2451493

[52] U.S. Cl.......................... 260/615 F; 260/614 F; 260/615 BF
[51] Int. Cl.².......................................... C07C 41/00
[58] Field of Search........ 260/614 F, 615 F, 615 BF

[56] References Cited
UNITED STATES PATENTS 3,242,218  3/1966  Miller........................... 260/615 BF
3,342,875  9/1967  Selman et al. ................ 260/615 BF
3,555,100  1/1971  Garth............................ 260/614 FY Primary Examiner—Howard T. Mars
Attorney, Agent, or Firm—Curtis, Morris & Safford

[57] ABSTRACT

Perfluorinated ethers containing carboxylic acid fluoride groups and optionally units derived from hexafluoropropene epoxide or tetrafluoroethylene epoxide are reacted with fluorine at temperatures of from 50° to 350°C in the presence of metallic catalysts. During the reaction carbonyl difluoride is splitt off and an ether is obtained in high yield which is free of carboxylic acid fluoride groups. Metallic silver is well suited as catalyst.

10 Claims, 1 Drawing Figure

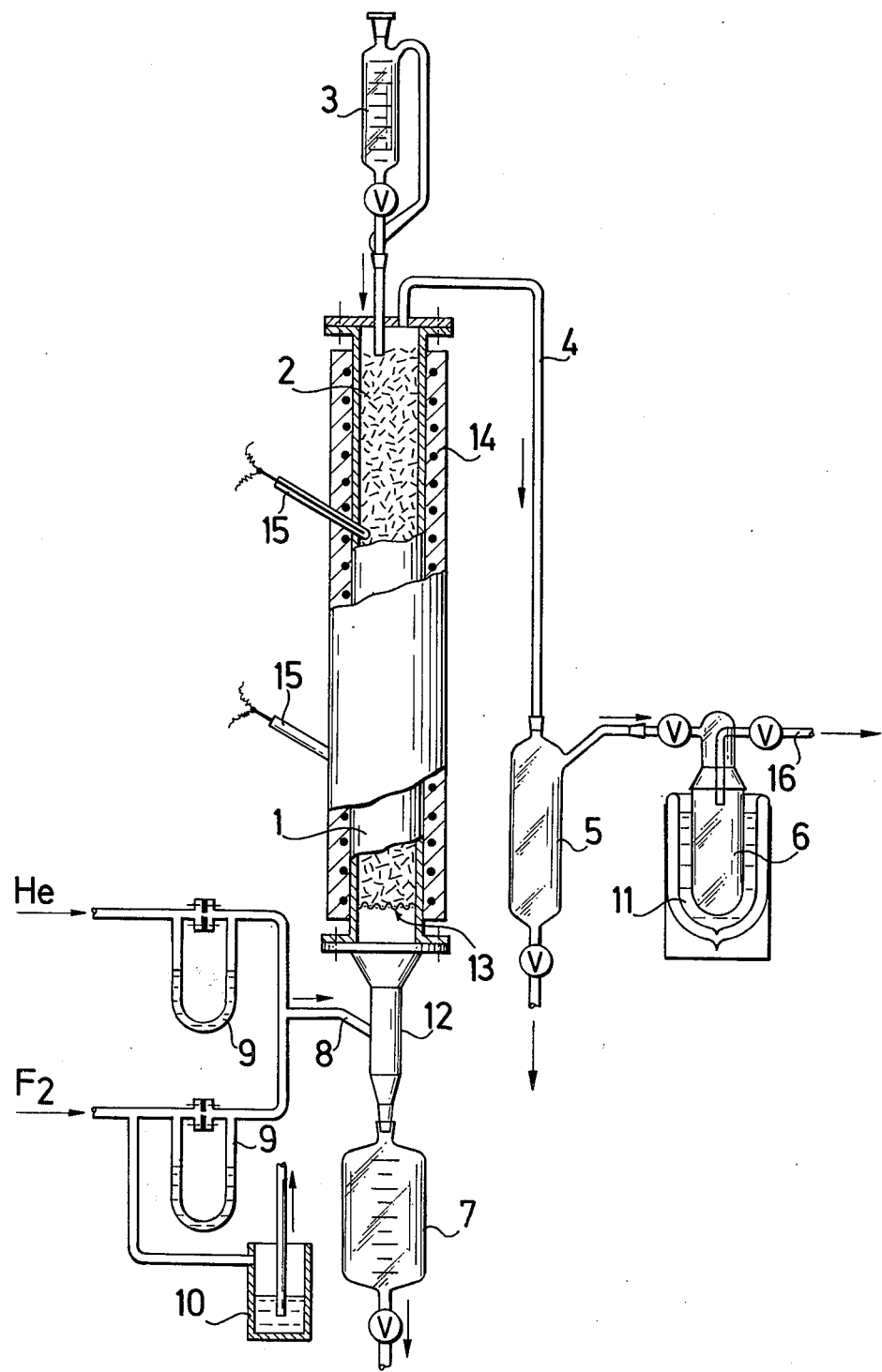

PROCESS FOR PREPARING PERFLUORINATED ETHERS

The present invention relates to the preparation of perfluorinated ethers, especially of polyethers. Polethers have a high thermal resistance, are inflammable and chemically stable even with regard to strong oxidants. Owing to their particular physical properties, for example, favorable viscosity in a wide temperature range, partly high boiling points and simultaneous low solidifying points, low surface tension, extreme dielectrical properties and high resistance to radiations, perfluorinated ethers may be used in a wide field of application as inert liquids, dielectrical agents, heat exchanging agents, hydraulic oils and lubricants, especially in the presence of highly aggressive media. There is, consequently, a need for economical and simple processes for preparing compounds of this class.

The corresponding perfluorinated polyethers having carboxylic acid fluoride terminal groups, which may be easily obtained, are suitable used as starting compounds for preparing perfluorinated polyethers. A decisive step for the preparation of the desired chemically inert and thermally stable compounds consists in eliminating these functional reactive terminal groups.

According to U.S. Pat. No. 3,342,875 the carboxylic acid obtained by hydrolysis from the corresponding acid fluorides of perfluorinated polyethers are converted into their salts and subsequently decarboxylated in the presence of alkaline media. In this way, however, only incompletely fluorinated terminal groups of the formula —CFRH, wherein R represents a fluorine atoms or $CF_3$, are obtained.

It is moreover known to fluorinate carboxylic acid terminal groups of perfluorinated polyethers with elementary fluorine (cf. U.S. Pat. No. 3,242,218). In this process the carboxyl group is replaced by a fluorine atom according to the following equation:

$$—CFR—COOH + F_2 \rightarrow —CF_2R + CO_2 + HF$$

(wherein R = F or $CF_3$)

This process requires saponifying of the acid fluorides obtainable in known manner and carefully drying of the carboxylic acid prepared, before the reaction with fluorine may be performed. As well in the saponification as in the fluorination hydrogen fluoride is obtained as a by-product.

It has moreover been proposed to react the acid fluoride without previous saponification by decarbonylation in the presence of antimony pentafluoride according to the equation:

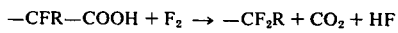

(cf. U.S. Pat. No. 3,555,100).

In this process fragmentation products may be performed, however, in a side reaction with antimony pentafluoride, which may reduce the yield. The residence time of the reactants is critical, especially at higher temperatures and should be as short as possible. In this process antimony pentafluoride and its by-products formed in the side reaction must be removed after the main reaction. This operation requires working up in an aqueous medium and leads, consequently, to a destruction of the valuable antimony pentafluoride catalyst. Problems simultaneously arise in the subsequent working up of the waste water. It is moreover necessary to dry the washed perfluorinated polyether. It is a feature of the invention to improve the process for splitting off by fluorination acid fluoride groups from perfluorinated compounds, especially perfluorinated ethers.

The present invention consequently relates to a process for preparing perfluorinated ethers of the formula

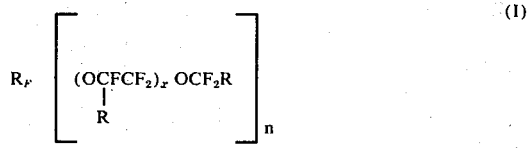

wherein
$R_F$ represents a radical of a perfluoroalkane having of from 1 to 19 carbon atoms and $n$ free valencies,
$n$ is 1 or 2,
R represents $CF_3$ or a fluorine atom and
X represents an integer of from 0 to 50,
which comprises reacting a carboxylic acid fluoride of the formula

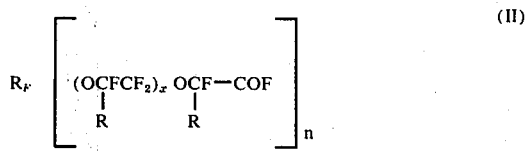

wherein
$R_F$, R, $x$ and $n$ have the aforesaid meaning, with elementary fluorine at temperatures of from +50° to +350° C in the presence of a metallic catalyst, containing at least one element selected of the group of magnesium, aluminium, tin, lead, bismuth, cerium, lanthanum, titanium, zirconium, chromium, manganese or of the group IB, IIB or VIII of the Periodic Table. The radical $R_F$ has $n$ free valencies. It may be linear, branched or cyclic and has from 1 to 19 carbon atoms. If $n$ is 1, $R_F$ preferably has from 1 to 8, especially of from 1 to 3 carbon atoms. If $n$ is 2, $R_F$ preferably has from 2 to 10, especially of from 3 to 5 carbon atoms.

Perfluorinated ethers wherein $x$ is from 5 to 35, inclusive are especially interesting because of their physical properties.

The reaction preferably is performed in the absence of inert diluents; the use of inert liquid solvents (for example of perfluoro-3-isopropyl-2-methyl-pentane) certainly is possible but is of no advantage, as they must be removed afterwards. The fluorine used may be diluted with inert gases such as nitrogen, helium, argon, carbon dioxide or tetrafluoromethane or be used in a pure undiluted form. The reaction is preferably carried out under anhydrous conditions in order to avoid the formation of hydrogen fluoride.

The reaction is carried out at temperatures of from +50° to +350° C. Temperatures of from +80° to +250°

C, especially of from 150° to 210° C are especially advantageous. The reaction may be carried out in the gaseous phase, especially when using low boiling starting products. One preferably works in the liquid phase, however. In this case the process generally is performed in an analogous manner to common gas-liquid reactions.

It is possible in a simple manner to introduce the carboxylic acid fluorides of formula II into an agitator flask, to add a metallic catalyst which may be e.g. pulverized, to heat the contents of the flask to the reaction temperature and then to react with gaseous dilute or undilute fluorine. The required amounts of metal are in the range of from 1 to 10% by weight, calculated on the compounds of formula II.

Semi-continuous and especially fully continuous methods are used preferably, however, especially such working with counter-current flow.

An especially simple and, consequently, preferred method consists in introducing dropwise the compounds of formula II into a vertical tube charged with metallic fillers at the top and in adding elementary fluorine in a gaseous state at the lower part of the tube. Thus the arrangement of a trickling tower is obtained. The sizes of the reaction tube are not critical for the course of the process according to the invention. A large surface of the metal having a catalytic effect is always of decisive importance. A height of 5, especially 10 to 50 times the inner diameter of the tube is preferably used. The inner diameter may be of from 10 to 1000, preferable of from 50 to 500 mm, depending on the output. Narrower tubes may be likewise used, naturally. The perfluorinated ether is collected at the lower end of the fluorination reactor; and the gaseous components are withdrawn at the upper end. Thus the requirements of a continuous working are fulfilled. The trickling tower may also work with parallel flow.

Another simple method consists in introducing the compound of formula II together with fluorine in an empty long tube in a parallel flow, while replacing the aforesaid metallic bodies by the wall of a metallic tube having a catalytic effect, and in withdrawing the reaction products at the other end of the pipe to separate them. The diameter of the latter pipe is in the range of from 1 to 10, preferably of from 2 to 5 mm. The proportion of the length and the inner diameter should be at least 1000:1, preferably from 2000 to 10,000:1.

When working continuously, the addition of fluorine is adjusted in dependence of the addition of carboxylic acid fluoride. It should at least correspond to the stoichiometric portions, i.e. equivalent quantities calculated on the compounds of formula II should be used. In order to assure a constant complete conversion of carboxylic acid fluoride, a low excess of fluorine, preferably of from 5 to 10%, is preferably introduced. In order to avoid waste gas problems thus arising it is advantageous in this case to provide after the first reaction tube a second tube of the same or similar construction. The second tube works with counter-current flow and is also fed with carboxylic acid fluoride. Unconsumed fluorine is converted therein. The mixture of the compounds of formulae I and II obtained in the second reaction tube may then be passed to the first reaction tube and be completely reacted therein.

The residence time of the polyether compound in the reactor may vary from some minutes to some hours; it depends on the viscosity and the flowing properties of the readily mobile to oily liquids used each time, on the nature of the metallic bodies used and especially on the reaction temperature. In order to obtain pure reaction products of formula I and to avoid thus considerable difficulties in the separation, the residence time should be such that a complete conversion is obtained.

As the perfluorinated polyethers formed in the fluorination are stable with regard to fluorine within the temperature range used, the residence time of the polyether in the reactor is not critical and its upper limit depends only on technical considerations.

The process is preferably carried out under atmospheric pressure, but may be performed under elevated pressure or under reduced pressure.

Any material sufficiently resistant with regard to fluorine and carboxylic acid fluorides may be used for the metallic content fed to the reaction tube, for example, steel, copper, platinum; the reactor may also be lined, for example, with polytetrafluoroethylene. If the fluorine is sufficiently free from hydrogen fluoride, the tube may also be advantageously made of glass, quartz or ceramics. Suitable catalytically acting metals are such of Group I B to VIII of the Periodic Table, which do not form volatile or liquid fluorides at the reaction temperature. Besides the catalytically acting metallic elements, alloys thereof may also be used, for example, copper-nickel alloys (German silver), copper-tin alloys (bronze), copper-zinc alloys (brass), silver-copper alloys (silver solder), cobalt-chromium alloys, or chromed steel. Coated metals such as silvered or gilded copper or platinized steel may also be used. Mercury is advantageously used in the form of amalgams, for example, of copper-amalgam.

The shape of the metallic body is not critical to the process; the metals may be present, for example, in the form of chips, spherules or cubes. Technically common filling bodies for distillation apparatus, such as, for example, Raschig rings, spirals, helices or saddles, however, are preferably used. The size of the filling bodies is not critical, provided that an adequate gas passage between the metallic bodies is assured. The volume of these bodies generally is in the range of from 1 mm³ to 1 cm³. Larger filling bodies may be used in technical plants. The principles of the distillation technique also apply to the proportion of the size of these filling bodies and the diameter of the reactor tube.

The process according to the invention may also be carried out with some limitations in the absence of metallic bodies, for example, by using glass helices. This reaction, however, is only incomplete at temperatures below 200° C. At temperatures above 200° C, a considerable fragmentation simultaneously is produced, which may cause problems in the separation or losses in the yield. By using metallic bodies the reaction temperature may be considerably reduced; this effect possibly may be attributed to the improved dissipation of the reaction heat by the metallic bodies and besides to the catalytic effect of the metallic surface or the metal fluorides formed thereon.

The nature of the surface is not critical, either. It may be smooth, slightly etched or porous.

The metals or the metallic bodies used in the process of the present invention may be used as such, but they are preferably contacted previously with elementary, preferably dilute fluorine, in an analogous manner to the process described in Example 1.

The carboxylic acid fluorides of the formula II may be easily obtained and are prepared from tetrafluoroethylene epoxide or hexafluoropropene epoxide according to known methods. In case that $R_F$ represents a perfluoroalkyl radical, the homopolymers of hexafluoropropene epoxide (wherein $R_F$ represents $C_3F_7$) or of tetrafluoroethylene epoxide (wherein $R_F$ represents $C_2F_5$) may be used as acid fluorides (cf. U.S. Pat. Nos. 3,250,808, 3,125,599). It is also possible to synthesize higher perfluoroether acid fluorides from perfluorocarboxylic acid fluorides and perfluoroepoxides (cf. German Pat. No. 1,234,702). In this process the reaction products with carbonyl fluoride, trifluoroacetyl fluoride and perfluoropropionyl fluoride, in which reaction products $R_F$ (of formula II) represents a perfluoroalkyl radical of from 1 to 3 carbon atoms, are especially interesting. Products wherein $R_F$ represents a branched perfluoroalkyl radical may be obtained by reacting perfluoromonoketones, for example, hexafluoroacetone with perfluoroepoxides (cf. U.S. Pat. No. 3,274,239). Bivalent perfluoroether acid fluorides may also be obtained according to the same principles. Polyether acid fluorides of the formula II, wherein $R_F$ represents the group $-CF_2CF_2-$ may be synthesized from perfluorodicarboxylic acid fluorides with perfluoroepoxide (cf. U.S. Pat. No. 3,250,807). These compounds are especially interesting, as oxalyl fluoride may be easily obtained. Higher perfluorinated homologues of oxalic acid fluoride, especially those having up to 10 carbon atoms may be used in an analogous manner. It has been found that branched perfluoroalkylene radicals of the formula $-CFR'-CFR'-$, wherein $R'$ represents a perfluoroalkyl radical of from 1 to 4 carbon atoms, may be introduced into polyesters, synthesis starting from perfluorinated 1.2-diketones, for example, by reacting them with hexafluoropropylene epoxide.

The reaction of the carboxylic acid fluorides of the formula II with fluorine leads to the corresponding ethers with splitting off of carbonyldifluoride according to the reaction:

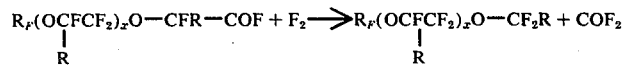

(wherein R represents F or $CF_3$)

The optimum reaction temperatures depend, not only on the chain length of the polyether compound used each time, but especially on the metal charge of the reactor. While silver or silvered copper already causes a complete fluorination or splitting off of the $-COF-$group at temperatures of from 90° to 95° C, temperatures of from about 170° to 190° C are required for the complete conversion of the same carbonyl acid fluoride in the presence of nickel.

The process according to the invention has the advantage that the reaction may already be carried out at very low temperatures, where side reactions, for example, the thermal splitting off of $COF_2$ from the group $-O-CF(CF_3)-COF$ with formation of perfluorovinyl ethers does not occur.

The conversions of carboxylic acid fluoride according to the reaction of the invention are quantitative when the optimum reaction temperature is maintained and when adequate catalytic metal packing is selected; the yields of the perfluorinated polyethers of formula I are nearly quantitative and are in the range of from 90 to 99% of the theory calculated on the carboxylic acid fluoride used (= converted), by taking into account the quantity of liquid adhering on the reactor material.

According to the process of the invention the compounds of formula I are obtained in the form of transparent colorless liquids which may be easily worked up. As the portion of fragmentation products is quite insignificant surprisingly, a separation by distillation may be dispensed with. A washing process with water is not required, but care must be taken that the reaction product is liberated from dissolved fluorine gas, which may be done by evacuation or by introducing inert gas in known manner. Compounds of formula I of a high molecular weight may also solidify at room temperature to give wax-like products.

The volatile reaction products, fluorophosgene and low boiling fragments may be collected in suitable recipient vessels.

It is surprising that carboxylic acid fluorides derived from perfluorinated ethers may be reacted in a high yield with fluorine in the presence of metals without previous saponification or without using the aggressive antimony pentafluoride, at medium temperatures.

This improvement in the preparation of the neutral perfluorinated ethers, especially of polyethers, which may be used as functional liquids, lubricating oils, sealing liquids signifies a considerable technical progress. Not only homogeneous perfluoroethers may be obtained from homogeneous perfluoroether carboxylic acid fluorides according to the process of the invention, but mixtures of perfluorinated ethers of the formula I may also be prepared when using mixtures of carboxylic acid fluorides of the formula II.

When $R_F$ in formula II represents a perfluoroalkylene radical and $n$ is 2, a bivalent acid fluoride is obtained. It is not necessary that both side chains of the formula $-(OCRFCF_2)_xOCRF-COF$ are identical, but the index $x$ of both side chains may be different, for example, as in the compound

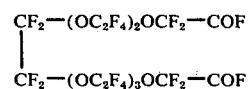

Diethers wherein $x$ is from 5 to 35, inclusive, especially those wherein $x_1 + x_2 \leq 35$, $x_1$ and $x_2$ representing (optionally different) indices x of both polyether side chains are of especial interest.

In acid fluorides of the formula

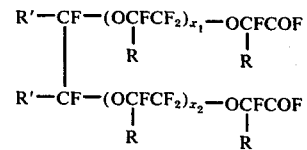

to be used according to the invention each $R'$ independent from one another, may represent a fluorine atom, or a perfluoroalkyl radical having of from 1 to 4 carbon atoms. Both radicals $R'$ are different, when unsymmetrical perfluorodiketones are used as starting compounds. Compounds wherein one radical R' represents a fluorine atom and the other a perfluoroalkyl radical may be prepared from perfluoro-α-ketocarboxylic acids.

The following examples illustrate the invention:

EXAMPLE 1

The test apparatus (the FIGURE) for fluorinating liquid carboxylic acid fluorides of formula II comprised a vertically arranged copper tube (1) having a length of 150 cm and an inner diameter of 5.3 cm. The tube was charged with silvered copper chips (2) (length from 20 to 40 mm, with from 4 to 6 mm, thickness from 0.3 to 0.6 mm), closed at its lower end by a sieve and heated by a heating jacket (14). The temperature inside the tube was measured by thermoelements (15). A dropping funnel (3) filled with carboxylic acid fluoride and a gas withdrawal tube (4) leading to a separator (5) for liquid cleavage products (medium boiler) followed by a glass trap (6) cooled by liquid nitrogen (11) for collecting the easily volatile reaction products (low boiler) were mounted at the top of the tube. Uncondensed gas portions were passed to the hood (16). A glass flask or receiver (7) was arranged after a Tee (12), at the lower end of the copper tube (1) where the high boiling perfluorinated polyethers of formula I were collected as transparent colorless liquids (high boilers). A copper conduit (8), through which dilute or undiluted fluorine could be introduced into the apparatus opened into the lateral part of the Tee (12).

Elementary fluorine ($F_2$) was taken from a commercial steel bottle, measured by means of a differential pressure flow meter (9) previously gauged and passed to the reactor after dilution with helium (He) or another inert gas. An ascending pipe manometer (10) simultaneously serving as a security valve was arranged before the fluorine flow meter for controlling the dynamic pressure produced. The pressure gages were fed with the perfluorinated polyether, the ground joints were sealed with Voltalef$^{(R)}$-grease, Graisse 90, (oligomers of polytrifluorochloroethylene) of the firm Ugine Kuhlmann. The reaction tube (1) filled with silvered copper chips (2) was heated to a temperature of from 200° to 205° C within 2 hours, while simultaneously passing a gas mixture through the pipe (8) consisting of fluorine and helium, initially in a proportion of $F_2$ : He of 1 : 4, thereafter, with an increasing fluorine content to a proportion of $F_2$ : He of 3 : 1. The surface of the metal chips thereby became tarnished and whitish. 439.6 g (about 0.14 mole) of dicarboxylic acid fluoride of the composition (III)

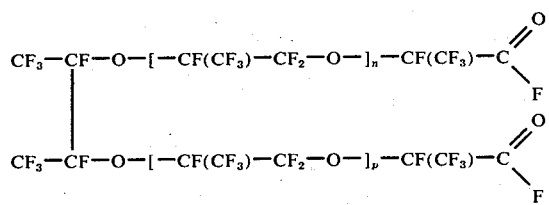

were then added dropwise at the same temperature in the course of 19.5 hours, at a rate of about 12 ml/h. A fluorine flow diluted with 0.2 l/h of helium was simultaneously passed through the tube (8) at a rate of 0.6 l/h. At the end of the test and after the oil had completely dropped off into the receiver (7) the following amounts of reaction products were weighed:

1. low boiling compounds in the glass trap (6) 22.1 g (without $F_2$)
2. medium boiling compounds in the separator (5) 2.5 g
3. high boiling compounds in the receiver (7) 417.3 g.

The low boiling compounds mostly were composed of carbonyldifluoride ($COF_2$) according to IR spectra. The remainder of the low boiling compounds as well as the medium boiling compounds were composed of short chain perfluoroether fragments. The high boiling compounds obtained initially were liberated in vacuo from the dissolved fluorine. According to $^{19}F$—NMR and IR-spectra the high boiling agents no longer contained carboxylic acid fluoride groups; even after having treated them with water (saponification) or with methanol (esterification) carboxylic acids or carboxylic acid esters could not be detected in the high boiling portions. The conversion of dicarboxylic acid fluorides used, consequently, was quantitative. In an additional distillation of the high boiling compounds in vacuo, 405 g of perfluoropolyether oil were obtained as the main fraction in a temperature range of from 185° to 280° C at a pressure of from 0.4 to 0.5 torrs. The yield of high boiling perfluoropolyether oil, consequently, was 93.8% of the theory, calculated on dicarboxylic acid fluoride used.

EXAMPLE 2

The carboxylic acid fluoride of formula III used in Example 1 was prepared in the following manner:

20 g of pulverized and dried cesium fluoride were suspended in 150 ml of absolute diethylene glycol dimethyl ether (diglyme). 30 g of hexafluorodiacetyl were added while cooling at a temperature of from −30°. After having stirred at 0° C for 5 hours, the CsF practically had completely disappeared while forming an addition compound with hexafluorodiacetyl. Then 1060 g of a gas mixture consisting of 70% of hexafluoropropene epoxide and 30% of hexafluoropropene were added while stirring in the course of 16 hours at a temperature of from −30° to −35° C. Unconsumed hexafluoropropene and some hexafluoropropene epoxide then were withdrawn in a gaseous state by slowly increasing the temperature and the remaining lower phase of the mixture consisting of two liquid phases was separated. Yield: 956 g.

508 g of an oily liquid boiling at a temperature in the range of from 200° to 290° C at a pressure of 0.5 torrs were obtained as main runnings by distillation after having withdrawn the first runnings boiling a temperature of from 50° C (at 760 torrs) and 200° C (at 0.5 torr). The elementary analysis, the determinations of the molecular weight and the terminal groups and the IR and the $^{19}F$—NMR-spectra revealed the following chemical structure of the dicarboxylic acid fluoride obtained:

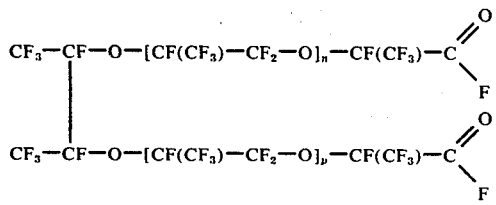

wherein $n + p = 13$ to 19, the average molar weight being about 3200.

EXAMPLE 3

The reaction tube fed with the same catalyst as in Example 1 was heated to a temperature of from 160° to 170° C, the test arrangement being the same as in Example 1.

In the course of 48 hours 422 g (about 0.21 mole) of dicarboxylic acid fluoride of Formula III and having been prepared in an analogous manner, but boiling in a temperature range of from 125° to 200° C at 0.3 torr, in contrast to the dicarboxylic acid fluoride used in Example 1, having an average molecular weight of 2000 and a composition wherein $n + p = 5$ to 13 were added dropwise at a rate of about 5 ml/h.

During the time of addition fluorine diluted with 0.2 l/h of nitrogen was introduced in a counter-current flow from the lower end of the reactor at a rate of 0.5 l/h.

At the end of the test and after having completely separated the oil, the following reaction products could be detected:

1. low boiling products 29.4%
2. medium boiling products 7.0%
3. high boiling products 381.5%

In $^{19}$F—NMR and IR spectra as well as in saponification and esterification tests the high boiling perfluoropolyethers proved to be completely free from carboxylic acid fluoride groups. An additional distillation yielded 376 g of a fraction boiling in a range of from 110° to 190° C (at 0.3 torr). The yield consequently, was 91.7% of the theory, calculated on dicarboxylic acid fluoride used.

EXAMPLE 4

In analogous manner to Example 3 the reaction tube (1) was heated to 90° to 95° C. 88 g (about 0.044 mole) of dicarboxylic acid fluoride having the composition of the dicarboxylic acid fluoride used in Example 3 were added dropwise in the course of 15.5 hours at a rate of about 3 ml/h. Undiluted fluorine was simultaneously introduced into the reactor at a rate of 0.4 l/h.

After having terminated the test and after having completely dropped off the oil, 0.5 g of medium boiling compounds were obtained in the separator and 83.6 g of high boiling compound in the receiving vessel, wherein carboxylic acid fluoride groups could not be detected. The conversion of dicarboxylic acid fluoride used was quantitative.

EXAMPLE 5

The test was carried out, by using an arrangement analogous to that of Example 1, not consisting of copper, however, but of a Duran$^{(R)}$ glass apparatus with standard ground joint, the heatable glass reactor tube of which was filled with silvered copper chips and had a length of 70 cm and an inner diameter of 2.5 cm. The test was carried out as in Example 1. 125 g (0.108 mole) of monocarboxylic acid fluoride of the formula

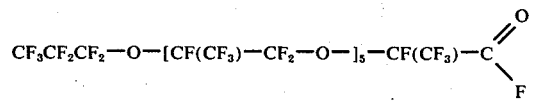

boiling in the range of from 55° to 67° C at 0.3 torr were added dropwise at a reactor temperature of from 150° to 155° C in the course of 22.5 hours.

A fluorine flow diluted with 0.2 l/h of nitrogen was simultaneously introduced at a rate of 0.6 l/h.

After having terminated the test 112.3 g of perfluoropolyether of the formula

had accumulated in the receiving vessel. Carboxylic acid fluoride groups could not be detected in the product obtained.

EXAMPLE 6

In the test arrangement of Example 5 the glass tube was charged with nickel chips instead of silvered copper chips. 89.6 g (0.045 mole) of dicarboxylic acid fluoride of the same composition as in Example 3 were added dropwise at a reactor temperature of from 185° to 190° C in the course of 22 hours, while a fluorine flow of 0.6 l/h, diluted with 0.2 l/h of nitrogen was simultaneously introduced. At the end of the test and after having completely separated the oil 85 g of perfluoropolyether oil had collected in the receiving vessel, which did not contain carboxylic acid fluoride groups. The conversion of dicarboxylic acid fluoride used was quantitative. The nickel chips did not manifest a visible modification.

EXAMPLE 7

The packing of the reaction tube was replaced by steel helices (composition 18% of chlorine, 8% of nickel, 74% of iron) while the test arrangement remained the same as in Example 5. In the course of 8 hours 40.3 g (0.02 mole) of dicarboxylic acid fluoride of Example 3 were added dropwise at a reactor temperature of from 160° to 170° C, while introducing simultaneously a fluorine flow of 0.8 l/h diluted with 0.3 l/h of nitrogen.

At the end of the test 34.8 g of perfluoropolyether oil had collected in the receiving vessel, which did not contain COF groups.

EXAMPLE 8

In the test apparatus according to Example 1 the reaction tube packed with silvered copper chips was heated to a temperature of from 210° to 215° C. 156 g of dicarboxylic acid fluoride of Formula III were added dropwise at a rate of about 10 ml/h in the course of 8 hours. The latter fluoride had been prepared in an analogous manner to Example 2 and been isolated from collected distillation residues. In contrast to the dicarboxylic acid fluoride used in Example 1 that used in Example 8 boiled at a temperature in the range of from 280° to 345° C at a pressure of from 0.02 to 0.04 torr. It had an average molecular weight of about 5000 and corresponded to the composition $n + p = 24$ to 30. During the time of addition fluorine diluted with 0.1 l/h of nitrogen was introduced in a counter current flow from the lower end of the reactor at a rate of 0.5 l/h.

At the end of the experiment and after having completely dropped off the highly viscous oil 122.4 g of high boiling substance were obtained (in the receiving vessel) and 5.8 g of medium boiling substance (in the separator). According to $^{19}$F—NMR and Ir-spectra the high boiling substances proved to be completely free from carboxylic acid fluoride groups.

EXAMPLE 9

The test was carried out with the same arrangement and by using the same catalyst as in Example 1. In the course of 7.5 hours 240.0 g of monocarboxylic acid fluoride of the formula

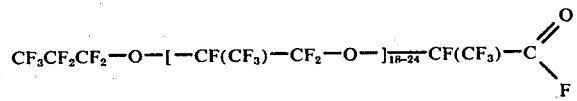

were added dropwise at a reaction temperature of from 190° to 200° C.

The acid fluoride had a boiling point of from 245° to 305° C at 0.4 torr. A fluorine flow diluted with 0.2 l/h of nitrogen was simultaneously introduced at a rate of 0.6 l/h. At the end of the test 223.6 g of perfluoropolyether of the formula

had collected in the receiving vessel. Carboxylic acid fluoride groups could not be detected in the product. A distillation carried out subsequently yielded a main fraction, having a weight of 195.1 g and boiling in the range of from 230° to 300° C at 0.4 torr.

EXAMPLE 10

The packing of the reactor tube was replaced by glass helices while the test arrangement remained the same as in Example 5. In the course of 6.5 hours 69.5 g of the dicarboxylic acid fluoride of Example 3 were introduced dropwise at a reactor temperature of from 202° to 208° C, while introducing simultaneously a fluorine flow diluted with 0.2 l/h of nitrogen at a rate of 0.6 l/h.

At the end of the test 41.3 g of liquid still containing carboxylic acid fluoride groups were obtained in the receiving vessel; the unreacted portion, calculated on dicarboxylic acid fluorides, was 6% by weight. 23.9 g of low boiling and high boiling substances were collected all together.

EXAMPLE 11

With the same test arrangement as in Example 1 the reaction tube fed with the same catalyst (silvered copper chips) was heated to a temperature of from 170° to 180° C. 126 g of dicarboxylic acid fluoride having the following structure

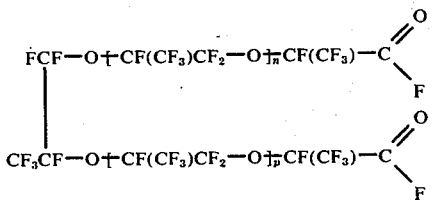

were added dropwise to a fluorine flow diluted with 0.2 l/h of nitrogen and introduced at a rate of 0.6 l/h. Said dicarboxylic acid fluoride was obtained in an analogous manner to the compounds of type III, by using instead of hexafluorodiacetyl (30 g) of Example 2 perfluorobenztartaric acid of the formula $CF_3COCOF$ (22.3 g). The subsequent polymerization reaction with hexafluoropropene epoxide and the working up of the dicarboxylic acid fluoride were effected as in Example 2.

A fraction of the dicarboxylic acid fluorides obtained boiling in a range of from 100° to 115° C at 0.3 torr was used for the fluorination reaction. The sum of the indices $n + p$ was in the range of from 8 to 10 and the average molecular weight was about 2000.

After having terminated the fluorination reaction and after having completely dropped off the oil 112.5 g of perfluoropolyether were collected in the receiving vessel as high boiling substance, not containing carboxylic acid fluoride groups. The conversion of dicarboxylic acid fluoride used was quantitative. The product obtained had the formula

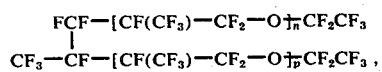

wherein $n + p$ was from 8 to 10.

EXAMPLE 12

The following acid fluorides could be reacted in similar manner according to the process of the invention.

| product used | product obtained |
| --- | --- |
| $C_2F_5O(C_2F_4O)_1CF_2COF$ | $C_2F_5O(C_2F_4O)_1CF_3$ |

-continued

| product used | product obtained |
|---|---|
| $C_2F_5O(C_2F_4O)_{31-45}CF_2COF$ | $C_2F_5O(C_2F_4O)_{31-45}CF_3$ |
| $(CF_2)_5\begin{matrix}O(C_2F_4O)_xCF_2COF\\O(C_2F_4O)_yCF_2COF\end{matrix}$ $x+y=4-8$ | $(CF_2)_5\begin{matrix}O(C_2F_4O)_xCF_3\\O(C_2F_4O)_yCF_3\end{matrix}$ $x+y=4-8$ |
| $(CF_3)_2CFO-CF_2-COF$ | $(CF_3)_2CFO-CF_3$ |
| $n\text{-}C_4F_9-O\left[\begin{matrix}CF_3\\|\\CF-CF_2O\end{matrix}\right]_{2-5}\begin{matrix}CF_3\\|\\CF-COF\end{matrix}$ | $n\text{-}C_4F_9-O\left[\begin{matrix}CF_3\\|\\CF-CF_2O\end{matrix}\right]_{2-5}C_2F_5$ |
| $C_8F_{17}-O-\begin{matrix}CF_3\\|\\CF-COF\end{matrix}$ | $C_8F_{17}O\ C_2F_5$ |
| $n\text{-}C_3F_7-O-\left[\begin{matrix}CF_3\\|\\CF-CF_2O\end{matrix}\right]_{8-11}\begin{matrix}CF_3\\|\\CF-COF\end{matrix}$ | $C_3F_7O-\left[\begin{matrix}CF_3\\|\\CF-CF_2O\end{matrix}\right]_{8-11}-C_2F_5$ |
| $CF_3-\begin{matrix}CF_3\\|\\CF\\|\\C_3F_7\end{matrix}-O-CF-COF$ | $CF_3-CFO-C_2F_5$ $|$ $C_3F_7$ |
| $C_2F_4\begin{matrix}O\ CF(CF_3)COF\\O\ CF(CF_3)COF\end{matrix}$ | $C_2F_4\begin{matrix}OC_2F_5\\OC_2F_5\end{matrix}$ |

What is claimed is:

1. Process for preparing perfluorinated ethers of the formula

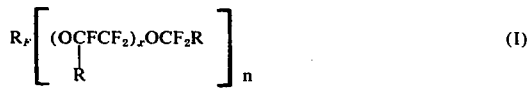 (I)

wherein
R$_F$ represents the radical of a perfluoroalkane having of from 1 to 19 carbon atoms and $n$ free valencies,
$n$ is 1 or 2,
R represents the groups CF$_3$ or F and
$x$ is an integer of from 0 to 50,
which comprises reacting a carboxylic acid fluoride of the formula

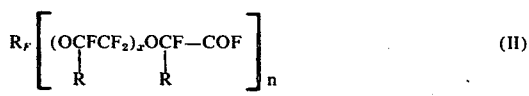 (II)

wherein R$_F$, R, $x$ and $n$ have the aforesaid meaning, at temperatures of from +50° to +350° C in the presence of a metallic catalyst comprising at least one metal selected from the group consisting of magnesium, tin, lead, bismuth, cerium, lanthanum, titanium, zirconium, chromium and manganese or at least one metal selected from groups IB, IIB or VIII of the Periodic Table, with elementary fluorine.

2. Process as claimed in claim 1, wherein $x$ is from 5 to 35, inclusive.

3. Process as claimed in claim 1, wherein R$_F$ represents a perfluoroalkyl radical having from 1 to 3 carbon atoms and $n$ is 1.

4. Process as claimed in claim 1, wherein R$_F$ represents a perfluoroalkylene radical having of from 2 to 10 carbon atoms and $n$ is 2.

5. Process as claimed in claim 4, in which R$_F$ is a perfluoroalkylene radical of the formula

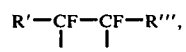

wherein R' and R''' each represent independent from one another a fluorine atom or a perfluoroalkyl radical having from 1 to 4 carbon atoms.

6. Process as claimed in claim 4, in which R$_F$ represents a perfluoroalkylene radical of the formula —CF$_2$—R''—CF$_2$—, wherein R'' represents a perfluoroalkylene radical having from 1 to 8 carbon atoms or a single bond.

7. Process as claimed in claim 1, which comprises operating at temperatures of from +80° to +250° C.

8. Process as claimed in claim 7, which comprises operating at temperatures of from +150° to +210° C.

9. Process as claimed in claim 1, which comprises using a metallic catalyst containing silver.

10. Process as claimed in claim 2, wherein R$_F$ represents a perfluoroalkyl radical having from 1 to 3 carbon atoms and $n$ is 1.

* * * * *